United States Patent [19]

Barth

[11] 3,934,000

[45] Jan. 20, 1976

[54] TOOTHPASTES

[75] Inventor: Jordan B. Barth, East Brunswick, N.J.

[73] Assignee: Colgate-Palmolive Company, New York, N.Y.

[22] Filed: Oct. 16, 1974

[21] Appl. No.: 515,272

Related U.S. Application Data

[63] Continuation-in-part of Ser. No. 301,934, Oct. 30, 1972, abandoned.

[52] U.S. Cl. .................................................. 424/49
[51] Int. Cl.$^2$ ......................................... A61K 7/16
[58] Field of Search ............................. 424/49–58

[56] References Cited
UNITED STATES PATENTS 3,538,230  11/1970  Pader et al............................ 424/50
3,703,578  11/1972  Cella et al............................ 424/49

OTHER PUBLICATIONS

Watson, J. Soc. Cosmet. Chem., Vol. 21, pp. 459–470, 1970.

*Primary Examiner*—Shep K. Rose
*Attorney, Agent, or Firm*—Robert L. Stone; Murray M. Grill; Herbert S. Sylvester

[57] ABSTRACT

A toothpaste containing a humectant, a silica thickener, a dental abrasive which is principally amorphous silica or an aluminosilicate, polyethylene glycol having an average molecular weight of about 500–700 and sodium carboxymethylcellulose having about 0.6–0.8 carboxymethyl groups per anhydroglucose unit.

5 Claims, No Drawings

TOOTHPASTES

This application is a continuation-in-part of copending U.S. Pat. application Ser. No. 301,934 filed Oct. 30, 1972, now abandoned.

Toothpastes conventionally comprise finely divided dental abrasives dispersed in humectant vehicles containing thickening and/or gelling agents.

One aspect of this invention relates to toothpastes of the type in which the vehicle comprises a humectant, sodium carboxymethylcellulose and a silica thickener and in which the dental abrasive is prinicipally (by weight) a finely divided material whose (empirical) $SiO_2$ content is at least 70%, whose particle size is about 2 to 20 microns, whose x-ray structure is essentially amorphous and whose index of refraction is about the same as that of the vehicle (e.g., about 1.43–1.48). Such toothpastes are known in the art, and are particularly useful when a transparent toothpaste is desired.

However, clear gel toothpastes as defined above present certain difficulties. The gel must be partially broken in order to extrude the ribbon from the tube. Consequently, it is essential for the extruded ribbon to be smooth and have adequate rigidity to retain its shape without flattening out and sinking into the bristles of the toothbrush. The toothpaste at the bottom of the toothbrush has little or no contact with the teeth and therefore has little cleaning and polishing effect on the teeth. The body (i.e., consistency) of the dental ribbon must be of sufficient thickness to be retained on the surface of the bristles and sufficiently cohesive so as not to ooze from its tube and so as to prevent any separation of liquid therefrom. Furthermore, desirable body character is necessary in order to permit tubes to be easily and satisfactorily filled during production. The retention of good body must exist during aging as well as during temperature and body of a clear gel toothpaste is important for manufacture production and consumer acceptance as well as cleaning performance.

Accordingly, it is an object of this invention to provide a transparent dentifrice possessing improved body and texture.

Another object of this invention is to provide a transparent dentifrice possessing improved cleansing performance.

In accordance with this invention it has been found that a vehicle containing polyethylene glycol having an average molecular weight of about 500–700, preferably about 550–650, and sodium carboxymethylcellulose having about 0.6 to 0.8 carboxymethyl groups per anhydroglucose unit significantly improves the body and texture of a transparent toothpaste. The use of this vehicle produces toothpastes which have very good body, are introduced easily into and extrude easily from a conventional toothpaste tube, retain a shiny appearance without visible dulling or hazy skin formation for considerable periods after extrusion, have a desirable short texture and are not undesirably stringy or grainy, and in general have outstanding rheological properties, coupled with good tooth cleaning, polishing and mouth feel characteristics and (in transparent types of toothpastes) good clarity.

Polyethylene glycols are well known in the art. The low molecular weight polyethylene glycols (i.e., 400 molecular weight) have been used in toothpastes which do not contain carboxymethylcellulose, as shown in U.S. Pat. No. 3,538,230. Similarly, high molecular weight polyethylene glycols (above 800 and preferably 1,000 – 6,000) have been used in toothpastes in order to obtain good texture, particularly with carboxymethylcellulose, as shown in U.S. Pat. No. 3,689,637. Surprisingly however, polyethylene glycols having an average molecular weight of about 600 have been found to be unpredictably unique in providing the superior body to dentrifices of instant invention. Polyethylene glycols of an average molecular weight below 500 as well as above 700 exhibit much less body, a thinner consistency and a flattened extruded ribbon. The use of this particular group of polyethylene glycols is clearly unexpected, since both the polyethylene glycols of lower molecular weights as well as those of greater molecular weight have substantially poorer body characteristics in clear gel toothpastes. As a matter of fact, the greater the molecular weight, the poorer the body and the lower the viscosity of the end product. The use of polyethyleneglycols of average molecular weight 600 have been found to be the only real way to improve the body of a carboxymethylcellulose containing clear gel formulation. Instant formulations have been found to be satisfactory after 9 weeks of accelerated aging tests.

The polyethylene glycols are mixtures of polymeric molecules of different degrees of polymerization; the graph showing the distribution of molecular weights (e.g., the graph plotting the degree of polymerization vs. per cent by weight) is typically a smooth "bell" shaped distribution curve. Thus a typical composition of a polyethylene glycol of average molecular weight about 600 (e.g., 570 to 630, corresponding to an average degree of polymerization of about 13–14) is as follows:

| D.P. | 6 | 7 | 8 | 9 | 10 | 11 | 12 | 13 | 14 | 15 |
|---|---|---|---|---|---|---|---|---|---|---|
| % | 0.5 | 1.5 | 3 | 4.8 | 6.1 | 7.8 | 9 | 10 | 11.5 | 11.5 |
| D.P. | 16 | 17 | 18 | 19 | 20 | 21 | 22 | 23 | 24 | |
| % | 11 | 9 | 5 | 3.5 | 2.6 | 2 | 1.3 | 0.8 | 0.8 | |

("D.P." means degree of polymerization, i.e., the number of ethylene oxide units in the molecule. "%" means percent by weight; the figures in the above tabulation are based on the graph of "Polymer Distribution in Carbowax polyethylene glycols..." in the 65 page booklet Carbowax Polyethylene Glycols F-4772E, published by Union Carbide Chemicals Company). It will be apparent that the proportion of materials of molecular weight 800 (D.P. 18) or higher is relatiely small, being below 25% and generally less than 20% of (e.g. about 16%) the total polyethylene glycol. In the most preferred formulations the proportion of materials of molecular weight 400 (D.P. 9) or lower is also relatively small, being below 25% and generally less than 20% (e.g., about 7%) of the total polyethylene glycol. Thus in these most preferred formulas at least half, by weight, of the polyethylene glycol molecules have molecular weights above 400 and below 800.

The proportion of the abrasive of high silica content is in the range of 5 to 50% of the composition, preferably about 10–30% such as about 15–25%. One abrasive is an amorphous alkali metal or alkaline earth metal aluminosilicate preferably having a refractive index of about 1.44–1.47, and containing at least about 70% silica, up to about 10% alumina, up to about 20% by weight of moisture and up to about 10% by weight of sodium oxide. Typically, this material has a particle size of up to about 35 microns, preferably about 1–20 microns, e.g. 2–4microns. The preferred moisture content is about 10–20% by weight, measured by loss at 1000°C. and the typical content of sodium oxide is about 5–10% by weight. Generally, the agent has a loose bulk density of up to about 0.2g/cc, such as about 0.07–0.12g/cc. Another suitable type of dental abrasive agent is porous amorphous silicic anydride having an average particle size preferable below 20 microns and above 1 micron, a surface area of at least about 200 m²/g, and preferably at leas about 300 m²/g and a bulk density of at least about 0.15 g/cm³ and preferably at least about 0.30 g/cm³, such as a dehydrated silica hydrogel (i.e., a xerogel), preferably of the well known regular density intermediate density type. Examples of such amorphous silicic anyhydride dental abrasives are Syloid 63, Syloid 72 and Syloid 74 which are described in "The Davison Family of Syloid Silicas" pubished by their manufacturer, Grace, Davison Chemical Company. Santocel 100, manufactured by Monsanto, is also a desirable dental abrasive. Syloid 72 has an average particle size of about 4 microns, a surface area of about 340 m²/g and a bulk density of about 1.77 g/cm³. Syloid 74 has an average particle size of about 8microns, and a surface area of about 320 m²/g and a bulk density of about 0.26 g/cm³. For Syloid 63 the corresponding figures are about 9 microns, about 675 m²/g and about 0.4 g/cm³. A grade of Santocel 100 has a surface area of about 239 m²/g and a bulk density of about 0.24 g/cm³. These amorphous silicic anhydrides may be used singly or in mixtures.

The proportion of the silica thickener is advantageously in the range of about 1 to 10%, preferably about 3 to 7%. The silica thickener may be silica gel (i.e., dehydrated silica hydrogel) of low bulk density such as a bulk density of below about 0.13g/cm³ e.g. 0.11 g/cm³, (e.g. Syloid 244 or Syloid 266). It may be a silica aerogel. Alternatively it may be a pyrogenic silica (e.g. Cab-O-Sil M5 or Aerosil D200).

The vehicle is made up primarily of a humectant such as glycerol or sorbitol, usually in admixture with water. Taken together, the proportion of these liquids in the toothpaste is advantageously in the range of about 40 to 90%, preferably about 60 to 80% and still more preferably about 65 to 76%. (Sorbitol, generally present in admixture with water, is considered as a liquid for this purpose). The water is preferably about 5 to 35%, more preferably about 15–20%, of the total liquids.

The proportion of sodium carboxymethylcellulose is preferably in the range of about 0.2 to 2%, still more preferably about 0.3 to 1%. One particularly preferred form has an average degree of polymerization in the neighborhood of 500, corresponding to a molecular weight in the neighborhood of 100,000. For instance one may use a material whose viscosity (of a 2% aqueous solution thereof at 25°C) is less than 3,000 centipoises, preferably below 1,000, e.g. about 300 – 600 centipoises, such as Hercules CMC-7MXF which has about 0.7 sodium carboxymethyl groups per anhydroglucose unit.

The proportion of polyethylene glycol of average molecular weight of about 500 – 700 is preferably in the range of about 1 to 20%, more preferably less than 10% such as about 2 to 4%.

The transparent toothpaste may also contain surface active agent, e.g., to achieve increased prophylactic action assist in achieving thorough and complete dispersion of the instant compositions throughout the oral cavity, and render instant compositions more cosmetically acceptable. The organic surface active material may be anionic, nonionic, ampholytic or cationic in nature, and it is preferred to employ as the surface active agent a detersive material which imparts to the composition detersive and foaming properties. Suitable types of such detergents are water soluble salts of higher faty acid monoglyceride monosulfates, such as sodium salt of the monosulfated monoglyceride of hydrogenated coconut oil fatty acids, higher alkyl sulfates, such as sodium lauryl sulfate, alkyl aryl sulfonate such as sodium dodecyl benzene sulfonate, higher alkyl sulfate acetates, higher fatty acid ester of 1,2 hydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium and ethanolamine salts of N-lauroyl, N-myristoyl, or N-palmitoyl sarcosine, which should be substantially free from soap or similar higher fatty acid material which tends to substantially reduce the effect of these compounds. The use of these sarcosine compounds in dentrifice compositions of the present invention is particularly advantageous since these materials exhibit a prolonged and marked effect in the inhibition of acid formation in the oral cavity due to carbohydrates breakdown in addition to exerting some reduction in the solubility of tooth enamel in acid solutions.

Other particularly suitable surface active materials include nonionic agents such as condensates of sorbitan monostearate with approximately 60 moles of ethylene oxide. condensates of ethylene oxide with propylene oxide condensates of propylene glycol ("Pluronics") and amphoteric agents such as quaternized imidazole derivatives, which are available under the trademark "Miranol" such as Miranol C₂M. Cationic surface active germicides and antibacterial compounds such as diisobutylphenoxyethoxyethyl dimethyl benzyl ammonium chloride, benzyl dimethyl stearyl ammonium chloride, tertiary amines, having one fatty alkyl group (of from 12 to 18 carbon atoms) and two (poly) oxyethylene groups attached to the nitrogen (typically containing a total of from about 2 to 50 ethanoxy groups per molecule) and salts thereof with acids, and compounds of the structure

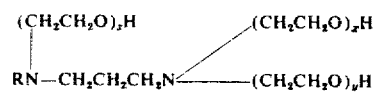

where R is a fatty alkyl group containing from about 12 to 18 carbon atoms, and $x$, $y$, and $z$ total 3 or higher, as well as salts thereof with mineral organic acids, may also be used. It is preferred that the total amount of surface-active agent be about 0.05–5% by weight, preferably about 1–3%, of the dentifrice.

Various other materials may be incorporated in the oral preparation of this invention. Examples thereof are coloring or whitening agents, preservatives, silicones, chlorophyll compounds, ammoniated materials, such as urea, diammoniumphosphate and mixtures thereof, and other constituents. Each of these adjuvants may be typically incorporated in the instant toothpastes in amount up to about 5%.

The toothpaste may also contain antibacterial agents in amounts of about 0.01–5%. Typical examples of such agents are guanidines, biguanides and amines such as:

$N^1$-(4-chlorobenzyl)-$N^5$-2,4-(dichlorobenzyl) biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidoxhexane;
1-(lauryldimethylammonium)-8-(p-chlorobenzyl-dimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine; and
their non-toxic acid additional salts.

Suitable flavoring or sweetening sialagogues may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, sorbitol, sodium cyclamate and saccharine. Suitably, flavor and sweetening agent may together comprise from about 0.01 to 5% or more of the compositions of the instant invention.

The compositions of the present invention suitably may also contain a fluorine-containing compound having a beneficial effect on the care and hygiene of the oral cavity, e.g. diminution of enamel solubility in acid and protection of the teeth against decay. Examples thereof include sodium fluoride, stannous fluoride, potassium fluoride, potassium stannous fluoride, ($SnF_2.KF$), sodium hexafluorostannate, stannous chlorofluoride, sodium fluorozirconate and sodium monofluorophosphate. These materials, which dissociate or release fluorine-containing ions in water, suitably may be present in an effective but non-toxic amount, usually within the range of about 0.01 to 1% by weight of the water-soluble fluorine content thereof.

The following Examples are given to illustrate this invention further. In this application all proportions are by weight unless otherwise indicated.

EXAMPLE 1

A transparent dental cream is prepared according to the following formulation: glycerine 25% sorbitol-water mixture (70% sorbitol-30% water) 42.83% sodium aluminosilicate 16%, silica thickener (low density silica gel) 5%, added water 3%, polyethylene glycol of average molecular weight 600 3%, sodium lauryl sulfite 2%, chloroform 1%, flavor (essential oil) 1%, sodium carboxymethylcellulose 0.35%, sodium benzoate 0.5%, sodium saccharin 0.17% coloring agent (1% aqueous solutions of F D & C Red No. 2 and F D & C Yellow No. 5) 0.15%.

The sodium aluminosilicate has the following empirical composition: silica about 72%, alumina about 8%, sodium oxide about 7%; water (ignition loss at 1000°C) about 12%. It has a bulk density of about 0.19–0.22 g/cm$^3$, a surface area of 120 m$^2$/g, a particle size of about 2 microns (the particles being aggregates of material of ultimate particle size of 35 millimicrons), an oil absorption value of 150–160 g/100g and a pH (for a 4% slurry in water) of about 10.5. The low density silica gel has a bulk density of about 0.11 g/cm$^3$, a particle size of about 4 microns, a surface area of 310 m$^2$/g, an oil absorption value of about 130 g/100g and a pH (for a 5% aqueous slurry) of 7.6. The sodium carboxymethycellulose is Hercules CMC-7MXF.

The mixture is made in the following manner, the gelling agent (sodium carboxymethyl cellulose) being dispersed in glycerine before the water or aqueous mixtures are added; a gel is formed, the abrasive is added and the whole mixture is deaerated (in vacuo) before it is placed in conventional collapsible toothpaste tubes. The tubes are stored at room temperature for several days before the product is tested.

The product extrudes easily as a ribbon from a toothpaste tube, has good body and is non-stringy and non-oozing; that is after a ribbon of the toothpaste is extruded, slow oozing of the material does not continue after the extrusion pressure has ended. It behaves well in automatic tube-filling equipment in which the toothpaste is extruded (intermittently) into successive collapsible tubes from a nozzle and in which it is desirable that there be no dripping or stringing from the nozzle after it leaves one tube and before it enters the next one. A ribbon of the product extruded from the tube maintains its clear shiny apperance for a considerable time.

After aging 6 weeks of 120°F in a toothpaste tube, the product maintains its desirable properties; its body and viscosity rise but it is still easily extrudable.

EXAMPLES 2 –4

Example 1 is repeated except that the following materials are used in place of the polyethylene glycol of 600 average molecular weight:

Ex. 2: polyethylene glycol of 950 – 1050 average molecular weight;
Ex. 3: polyethylene glycol of 1300 – 1600 average molecular weight;
Ex. 4: polyethylene glycol of 15,000 – 20,000 average molecular weight.

Table I

| Product | Initial Viscosity | Ribbon Shape | Aged Viscosity (6 weeks at 120°C) |
|---------|-------------------|--------------|-----------------------------------|
| Ex 1    | 55.0              |              | 71.6                              |
| Ex 2    | 43.7              | (Rounded)    | 39.0                              |
| Ex 3    | 37.9              | (Flattened)  | 39.4                              |
| Ex 4    | less viscosity; drying out at the neck end | (Still Flatter) | — |

In each case the extruded ribbon has much less body than that of Example 1; it is flatter and not as thick; and its Brookfield viscosity (as measured with a model RBF Brookfield viscometer at 10 RPM using spindle No. 7) is less. Optimum viscosity for this type of dental cream is about 50–70. The higher the molecular weight the lower the body and the viscosity of the material. The product of Example 4 has the lowest viscosity and poorest body and the extruded ribbon shows a marked loss of gloss, or dryness. The differences in body are marked and thus can be detected simply by placing one's finger on the extruded ribbon and drawing it away.

EXAMPLE 5

Example 1 is repeated except that a polyethylene glycol of 400 average molecular weight is used in lieu of the polyethylene glycol of 600 average molecular weight.

A ribbon of this dentifrice extruded from a tube having an orifice of 0.22 inches diameter had a width of 0.367 inches as compared to a ribbon width of 0.305 inches for a dentrifice prepared in accordance with Example 1. Thus it is apparent that the width of this ribbon is .147 inches wider than the orifice, whereas the width of the ribbon of the dentifrice of Example 1 is only .085 inches wider than the orifice. The fact that the instant the ribbon expanded and flattened to a greater extent is indicative of much less body, flatter and not as thick body and less viscosity.

The product of Example 1 clearly possesses superior rheological characteristics over the products of Examples 2 - 5 inclusive.

EXAMPLE 6

Example 1 is repeated except that the proportion of sodium aluminosilicate is increased to 18%, the proportion of silica thickener is increased to 7%, the proportion of sorbitol-water mixture is reduced to 38.83% and the sodium aluminosilicate has the following empirical composition: silica about 78%; alumina about 1%; sodium oxide about 10%, water (determined by loss on ignition at 1000°C) about 10%. It has a surface area of about 225–300 m²/g, an oil absorption of about 80–100 g/100g, a particle size of about 2 to 4 microns and a pH (measured on a 4% slurry in water) 7.5.

EXAMPLE 7

This Example illustrates the use of the toothpaste of this invention in combination with small proportions (e.g., about ½ to 1% of each) dispersed finely divided zirconium silicate (having an average particle diameter in the range of about 0.3 to 1 micron and essentially free of particles above about 5 microns in diameter) and iridescent flakes, to produce a toothpaste of unique subdued sparkling and pearlescent appearance having a beneficial effect on the dentition, e.g., polishing the enamel. The toothpaste is prepared from the following ingredients: glycerine 25 parts, sorbitol-water mixture (70% sorbitol 30% water) 41.8 parts, sodium aluminosilicate of Example 1 16 parts, low density silica gel of Example 1 4 parts, deionized water 3 parts, polyethylene glycol of 600 average molecular weight 3 parts, sodium lauryl sulfate 2 parts, chloroform 1 part, zirconium silicate 1 part, titanium dioxide-coated mica flakes 1 part, the sodium carboxymethylcellulose of Example 1 0.35 part, sodium benzoate 0.5 part, sodium saccharin 0.17 part, flavor (essential oil) 1 part, 1% aqueous solution of F D & C yellow No. 5 0.09 part, 1% aqueous solution of F D & C Blue No. 1, 0.09 part. The zirconium silicate particles have the following particle distribution: 100% below 4 microns, 99% below 2.5 microns, 94% below 2 microns, 72% below 1 micron, 46% below 0.5 micron, 27% below 0.3 micron, 3% below 0.2 micron (Ultrox 1000W). The titanium dioxide-coated mica flakes (Timica Sparkle) range in size from about 15–40 microns; their thickness is about 0.7 microns; their titanium dioxide coatings (on both faces of each flake) are of anatase; and their composition is about 20% anatase, 80% mica.

EXAMPLE 8

Example 7 is repeated except that the proportion of zirconium silicate is reduced to 0.5% and the proportion of titanium dioxide-coated mica flakes to 0.6% with corresponding increase in the proportion of sorbitol-water mixture It is understood that the foregoing description is given merely by way of illustration and that variations may be made therein without departing from the spirit of the invention. The "Abstract" given above is merely for the convenience of technical searches and is not to be given any weight with respect to the scope of the invention.

I claim:

1. A transparent toothpaste having improved body and texture, comprising a dental vehicle of aqueous humectant; about 3–7% silica thickeners; about 5–50% dental abrasive having an empirical $SiO_2$ content of at least 70%, a particle size of about 2 to 20 microns, an essentially amorphous X-ray structure, and an index of refraction which is about the same as that of the vehicle; said vehicle containing about 0.2–2% sodium carboxymethylcellulose having about 0.6 to 0.8 carboxymethyl groups per anhydroglucose unit, and about 1–10% polyethylene glycol having an average molecular weight of about 550–650, the graph of its molecular weight distribution being a bell-shaped curve, at least one-half by weight of said polyethylene glycol being molecular weights above 400 and below 800.

2. A transparent toothpaste in accordance with claim 1, wherein the dental abrasive is an alkali metal aluminosilicate.

3. A toothpaste in accordance with claim 2, wherein the humectant is selected from the group consisting of glycerol, sorbitol, and mixtures thereof.

4. A toothpaste according to claim 2, wherein the polyethylene has an average molecular weight of about 570 to 630.

5. A toothpaste according to claim 1, which also contains a minor amount of a surface active agent.

* * * * *